(12) United States Patent
Wang et al.

(10) Patent No.: US 9,610,580 B2
(45) Date of Patent: Apr. 4, 2017

(54) MAGNETICALLY TUNABLE MICROSTRUCTURED SURFACES

(71) Applicants: Evelyn N. Wang, Cambridge, MA (US); Yangying Zhu, Cambridge, MA (US); Rong Xiao, Houston, TX (US)

(72) Inventors: Evelyn N. Wang, Cambridge, MA (US); Yangying Zhu, Cambridge, MA (US); Rong Xiao, Houston, TX (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 464 days.

(21) Appl. No.: 14/294,829

(22) Filed: Jun. 3, 2014

(65) Prior Publication Data

US 2014/0352382 A1 Dec. 4, 2014

Related U.S. Application Data

(60) Provisional application No. 61/830,317, filed on Jun. 3, 2013.

(51) Int. Cl.
| | |
|---|---|
| *H01L 21/44* | (2006.01) |
| *B01L 3/00* | (2006.01) |
| *B41F 5/24* | (2006.01) |
| *H01L 29/40* | (2006.01) |
| *B41K 3/62* | (2006.01) |
| *C12M 1/42* | (2006.01) |
| *B23B 3/10* | (2006.01) |
| *C12M 1/12* | (2006.01) |
| *B23B 27/20* | (2006.01) |
| *H01F 1/00* | (2006.01) |

(52) U.S. Cl.
CPC ... *B01L 3/502761* (2013.01); *B01L 3/502792* (2013.01); *B23B 3/10* (2013.01); *B23B 27/20* (2013.01); *B41F 5/24* (2013.01); *B41K 3/62* (2013.01); *C12M 1/12* (2013.01); *C12M 1/42* (2013.01); *H01F 1/0072* (2013.01); *H01L 21/44* (2013.01); *H01L 29/40* (2013.01); *B01L 2200/0647* (2013.01); *B01L 2300/0816* (2013.01); *B01L 2300/123* (2013.01); *B01L 2400/0484* (2013.01); *Y10T 428/24917* (2015.01)

(58) Field of Classification Search
CPC ... C12M 1/12; C12M 1/42; B41K 3/62; B41F 5/24; H01L 21/44; H01L 29/40; B32B 3/10; B32B 27/40; B23B 27/20; B01L 3/502761; B01L 3/502792; B01L 2200/0647; B01L 2300/0816; B01L 2300/123; B01L 2400/0484; Y10T 428/24917; H01F 1/0072
USPC ........................................................ 428/209
See application file for complete search history.

(56) References Cited

U.S. PATENT DOCUMENTS

| | | | |
|---|---|---|---|
| 8,148,264 B2 * | 4/2012 | Henry ................. | B81C 1/00111 257/775 |
| 2010/0098941 A1 * | 4/2010 | Moon ...................... | C08J 7/123 428/339 |

(Continued)

*Primary Examiner* — David B Jones
(74) *Attorney, Agent, or Firm* — Foley & Lardner LLP

(57) ABSTRACT

Provided in one embodiment is a dynamically tunable structure including an elastic layer, and a plurality of ferromagnetic micropillars disposed over the elastic layer. The elastic layer may have an elasticity that is greater than an elasticity of the micropillars.

20 Claims, 16 Drawing Sheets

(56) References Cited

U.S. PATENT DOCUMENTS

| | | | |
|---|---|---|---|
| 2014/0352382 A1* | 12/2014 | Wang | B01L 3/502761 72/54 |
| 2016/0075987 A1* | 3/2016 | Zhang | C12M 23/26 435/395 |
| 2016/0152059 A1* | 6/2016 | Hart | B41F 5/24 101/333 |
| 2016/0167331 A1* | 6/2016 | Yang | C09J 163/00 428/206 |
| 2016/0213269 A1* | 7/2016 | Lam | A61B 5/0408 |

* cited by examiner

MAGNETICALLY TUNABLE MICROSTRUCTURED SURFACES

CROSS-REFERENCE TO RELATED PATENT APPLICATIONS

This application claims the benefit of and priority to U.S. Provisional Patent Application No. 61/830,317 filed on Jun. 3, 2013, the disclosure of which is incorporated herein by reference in its entirety.

STATEMENT REGARDING FEDERALLY SPONSORED RESEARCH

This invention was made with government support under Grant Nos. FA9550-11-1-0059 awarded by the Air Force Office of Scientific Research and N000140-91-10-0-0 awarded by the Office of Naval Research. The United States government has certain rights in this invention.

BACKGROUND

Micro and nanostructured surfaces have broad applications ranging from liquid transport in microfluidics, cell manipulation in biological systems, to light tuning in optical applications. While significant efforts have focused on fabricating various static micro and nanostructures with asymmetric features, dynamically tunable structures may extend manipulation capability in these systems. For example, pH/temperature-sensitive hydrogels that contract or swell in response to a stimulus have been used to deform microstructures and serve as an 'on/off' switch for chemical reactions. However, this approach is limited because hydrogels generally need a liquid environment for actuation. On the other hand, magnetic manipulation is particularly attractive due to the non-intrusive nature of magnetic fields. For example, PDMS micropillars containing cobalt nanoparticles embedded in the PDMS matrix have been used to apply forces to living cells, leading to different cellular reactions. However, the low loading of magnetic particles in the polymer matrix produces low magnetic strength, and the micropillar deflection is non-uniform. Due to the difficulty in fabrication, uniform arrays with well-controlled dynamic tunability have not yet been demonstrated, which dynamic tunability would offer additional manipulation capability in these various systems.

SUMMARY

In view of the foregoing, the Inventors have recognized and appreciated the advantages of a fabrication process for the development of magnetically tunable uniform micropillar arrays, where the tilt angle and direction can be controlled upon application of an external magnetic field. Furthermore, this fabrication approach is easily repeatable and scalable to large areas with uniform pillar arrays greater than 1 cm$^2$.

Accordingly, provided in one embodiment is a structure including an elastic layer, and a plurality of ferromagnetic micropillars disposed over the elastic layer. The elastic layer may have an elasticity that is greater than an elasticity of the micropillars.

Provided in another embodiment is a method of producing a structure, the method including patterning a photoresist disposed over a substrate to form a template, disposing a ferromagnetic material over the substrate to form micropillars comprising the ferromagnetic material, removing the photoresist, bonding the micropillars to an elastic layer, and removing the substrate. The elastic layer may have an elasticity that is greater than an elasticity of the micropillars.

Provided in another embodiment is a method including applying a magnetic field to a structure, wherein the structure includes a plurality of ferromagnetic micropillars disposed over an elastic layer, to change a tilt angle of at least some of the micropillars relative to a normal of the elastic layer. The elastic layer may have an elasticity that is greater than an elasticity of the micropillars.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
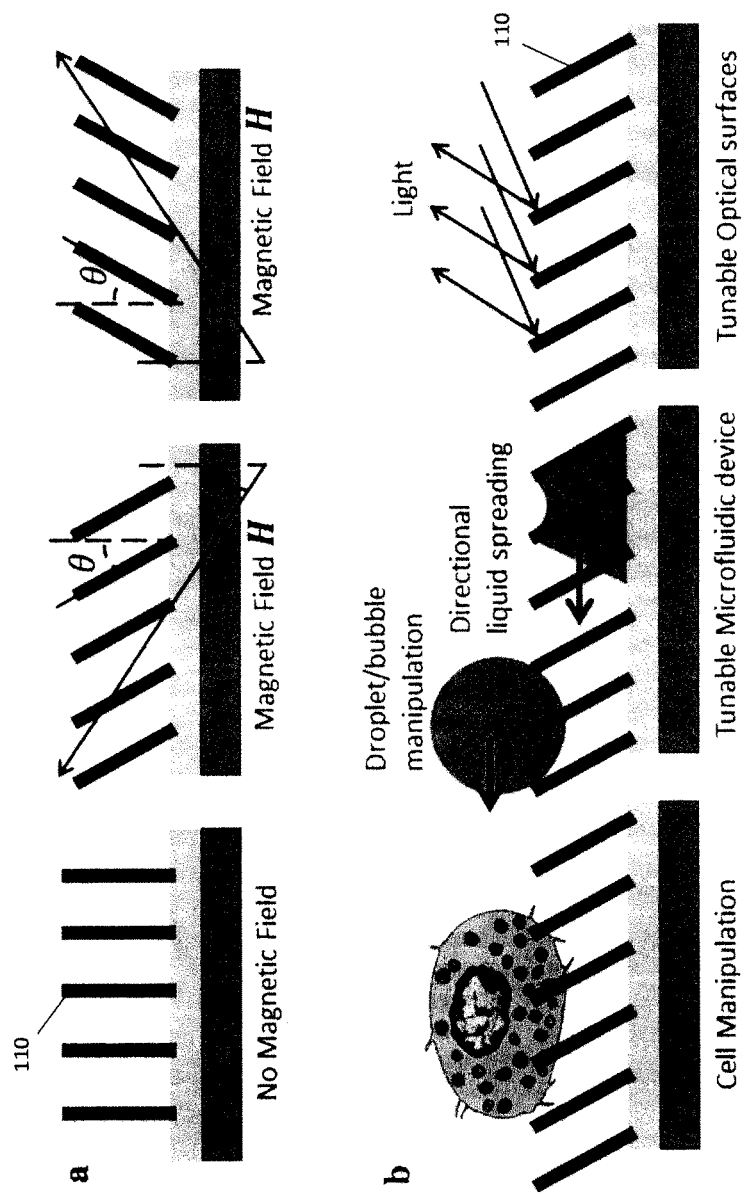
FIGS. 1(a) and 1(b) are schematics showing the concept of magnetically tunable micropillar arrays according to one embodiment, where the tilt angles may be controlled via an external magnetic field, and various potential applications including cell, microfluidic and light manipulation, respectively.

Following below are more detailed descriptions of various concepts related to, and embodiments of, magnetically tunable micropillar structures and methods of fabricating and using the same. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Dynamically tunable micropillar arrays with uniform, reversible, continuous and extreme tilt angles with precise control for real-time fluid and optical manipulation are provided in one embodiment herein. Inspired by hair and motile cilia on animal skin and plant leaves for locomotion, liquid transportation and thermal-optical regulation, the flexible uniform responsive microstructures (μFUR) provided herein comprises a passive thin elastic skin and active ferromagnetic micropillars whose orientation is controlled by a magnetic field. Uniform tilt angles ranging from 0° to 57° were experimentally shown, and a model was developed to accurately capture the tilting behavior. Furthermore, the μFUR may control and change liquid spreading direction on demand, manipulate fluid drag, and tune optical transmittance over a large range. The versatile surface developed enables new opportunities for real-time fluid control, cell manipulation, drag reduction and optical tuning in a variety of important engineering systems, including applications that require manipulation of both fluid and optical functions.

Dynamically tunable structured surfaces offer new manipulation capabilities in mechanical, fluidic, and optical systems. Examples from nature have inspired the design of such active systems, for example bacteria use flagella as propellers and motile cilia in the lining of human respiratory airways move mucus and dirt out of the lungs. These biological systems may display well-defined structural patterns and controllable mechanical motion in response to different stimuli. Accordingly, the fabrication of tunable microstructures including temperature-sensitive liquid crystalline and thermoplastic elastomers, hydrogels that respond to thermal, chemical or optical stimuli, and polymer-based magnetically actuated structures has been investigated. However, the response of the thermally actuated elastomer is either irreversible or slow and the hydrogels require a liquid environment and have a long response time, thus limiting their applications.

Magnetically actuated surfaces are attractive due to their instantaneous response and the non-intrusive nature of magnetic fields. Previously reported approaches utilize magnetic particles mixed with or encapsulated by soft materials to form microstructures that deflect in an external magnetic field. These pre-existing composite surfaces have been used to apply forces to living cells for different cellular reactions, generate rotational and translational fluid movements in microfluidics, as well as manipulate and mix droplets. However, due to the low magnetic strength of pre-existing composite surfaces, which is limited by the volume fraction of particles in the polymer matrix, the tilt angles produces are small and non-uniform. Thus, the tuning capability of pre-existing composite structures has generally been limited to on-off control, as opposed to a continuous tuning range which is more desirable.

A flexible uniform responsive microstructure (μFUR) allows reversible uniform tilt angle control in response to an applied external magnetic field. The structure of the μFUR may include an elastic layer and a plurality of ferromagnetic micropillars. The elastic layer may have an elasticity that is greater than the elasticity of the ferromagnetic pillars.

The ferromagnetic micropillars may comprise any suitable including a ferromagnetic material. According to one embodiment, the ferromagnetic micropillars may include a metal, such as at least one of nickel, cobalt, and iron. The ferromagnetic micropillars may also include an alloy of the aforementioned metals. The micropillars need not be ferromagnetic. According to another embodiment, the micropillars may comprise any magnetic material. The ferromagnetic micropillars may have a homogeneous composition. According to one embodiment, a homogeneous composition may refer to a composition including a single phase. For example, a composite material that includes two or more constituent components/phases would not be considered a homogenous composition. In some instances, an oxide of the aforementioned metals may be included in the micropillars. In one embodiment, a thin oxide layer on the surface of the ferromagnetic micropillars will not be considered to render the micropillars non-homogeneous. According to one embodiment, the micropillars may exhibit uniform volumetric magnetization.

The ferromagnetic micropillars may have any suitable geometry. According to one embodiment, a micropillar may refer to a monolithic structure with an aspect ratio of at least about 2. The aspect ratio of the micropillars may be at least about 2—e.g., at least about 2.5, about 2.75, about 3.0, about 3.25, about 3.5 or more. According to one embodiment, the micropillars may have any suitable geometry. The micropillars may have a cross-section selected from at least one of a square, rectangular, star, ellipsis, circle, and other polygons. The cross section may also be a circle and thus, according to one embodiment, the micropillars may be cylindrical. According to another embodiment, the micropillars may have pointed tips. The cross section may also be of an irregular shape.

The ferromagnetic micropillars may have any suitable size. According to one embodiment, the micropillars may have at least one dimension in the range of about 0.1 µm to about 1000 µm. Depending on the context, the dimension may refer to height, diameter, and the like. The micropillars may have a height of less than or equal to about 100 microns. For example, the height may be about 50 µm to about 90 µm—e.g., about 55 µm to about 85 µm, about 60 to about 80 µm, or about 65 µm to about 75 µm. According to one embodiment, the micropillars have a height of less than about 100 µm—e.g., less than about 95 µm, about 90 µm, about 85 µm, about 80 µm, about 75 µm, about 70 µm, about 65 µm, about 60 µm, about 55 µm, about 50 µm, or less. A smaller or a larger height value is also possible. The micropillars may have a diameter of less than or equal to about 100 microns. The micropillars may have a diameter of about 20 µm to about 40 µm—e.g., about 25 µm to about 35 µm. According to one embodiment, the micropillars may have a diameter of less than about 100 µm—e.g., less than about 95 µm, about 90 µm, about 85 µm, about 80 µm, about 75 µm, about 70 µm, about 65 µm, about 60 µm, about 55 µm, about 50 µm, about 45 µm, about 40 µm, about 35 µm, about 30 µm, about 25 µm, about 20 µm, or less. A smaller or a larger diameter value is also possible.

The ferromagnetic micropillars may be arranged in an array of any suitable geometry. The array may be a one dimensional array (in a line) or a two dimensional array (in a plane). According to one embodiment, the ferromagnetic micropillars may be in a periodic array. In an alternative embodiment, the ferromagnetic micropillars may be arranged in a non-uniform and/or non-periodic pattern. The array may include a micropillar to micropillar spacing of about 50 µm to about 70 µm—e.g., about 55 µm to about 65 µm. According to one embodiment, the micropillar to micropillar spacing may be about 60 µm. Other spacing values may be possible. According to another embodiment, the micropillar to micropillar spacing may be larger than the diameter of the micropillars. The spacing in one embodiment may refer to a micropillar center to center spacing.

The elastic layer may be any suitable material with an elasticity greater than the elasticity of the ferromagnetic micropillars. According to one embodiment, the elastic layer may include a polymer. The elastic layer may include polydimethylsiloxane (PDMS). According to one embodiment the elastic layer has a different chemical composition than the micropillars. The elastic layer and the micropillars may exhibit decoupled material properties and capabilities. According to one embodiment, the elastic layer is non-magnetic.

The µFUR may be produced by any suitable process. According to one embodiment, the fabrication may include patterning a photoresist disposed over a substrate to form a template, disposing a ferromagnetic material over the substrate to form micropillars comprising the ferromagnetic material, removing the photoresist, bonding the micropillars to an elastic layer, and removing the substrate.

The substrate may comprise, or be, any suitable material, such as silicon. Prior to disposing a photoresist over the substrate a seed layer may be disposed over the substrate. The seed layer may include an adhesion layer and a main seed layer. The adhesion layer may be any suitable material, such as titanium. The main seed layer may be any suitable material, such as gold. According to one embodiment, the micropillars may be removed from the substrate by removing the seed layer, such as by etching the seed layer. Alternatively, the main seed layer may be disposed over the substrate in the absence of an adhesion layer. The adhesion layer may be disposed over the substrate in the absence of a main seed layer.

The fabrication may additionally (and optionally) include thermally annealing the micropillars. Thermal annealing may enhance the magnetic performance of the micropillars. The thermal annealing may be performed under a magnetic field, such as one that is perpendicular to the sample surface.

The bonding of the micropillars to the elastic layer may be achieved through any suitable process. According to one embodiment, the bonding may include the disposition of an adhesion layer on the free end of the micropillars attached to the substrate, such as a silica adhesion layer. The silica adhesion layer may facilitate the bonding of the micropillars to the elastic layer.

The elastic layer may be formed by any suitable process. According to one embodiment, the elastic layer may be formed on a substrate, such as a glass substrate. The substrate over which the elastic layer is formed may be a flexible substrate.

The ferromagnetic material may be disposed over the substrate by any suitable process. According to one embodiment, the ferromagnetic material may be disposed by an electroplating process, a chemical vapor deposition (CVD) process, a plasma vapor deposition (PVD) process, an electroless plating process, or combinations thereof.

The tilt angle of the micropillars of the µFUR may be changed by applying a magnetic field to the µFUR. According to one embodiment, the tilt angle of the micropillars refers to the angle of the micropillars relative to a normal of the elastic layer surface. The tilt angle of the micropillars may be any suitable angle. According to one embodiment, the tilt angle may be about 0° to about 60°—e.g., about 5° to about 55°, about 10° to about 50°, about 15° to about 45°, about 20° to about 40°, or about 25° to about 35°. The tilt angle may be at least about 5°—e.g., at least about 10°, about 15°, about 20°, about 25°, about 30°, about 35°, about 40°, about 45°, about 50°, about 55°, about 60°, or more. Other tilt angle values are also possible.

The magnetic field may have any appropriate field strength. According to one embodiment, the magnetic field strength may be at least about 0.2 T—e.g., at least about 0.3 T, about 0.35 T, about 0.4 T, about 0.5 T, about 0.6 T, about 0.65 T, about 0.7 T, about 0.8 T, about 0.9 T, about 1.0 T, or more. The magnetic field may be applied at any appropriate angle to the normal of the elastic layer surface. According to one embodiment, the absolute magnetic field angle may be at least about 10°—e.g., at least about 20°, about 30°, about 40°, about 50°, about 60°, about 70°, about 80°, about 90°, about 95°, or more. The magnetic field angle may be about 0° to about 90°—e.g., about 10° to about 80°, about 20° to about 70°, about 30° to about 60°, or about 40° to about 50°. According to one embodiment, the magnetic field angle may be about 0° to about 60° relative to the normal of the elastic layer surface.

Figure 7:
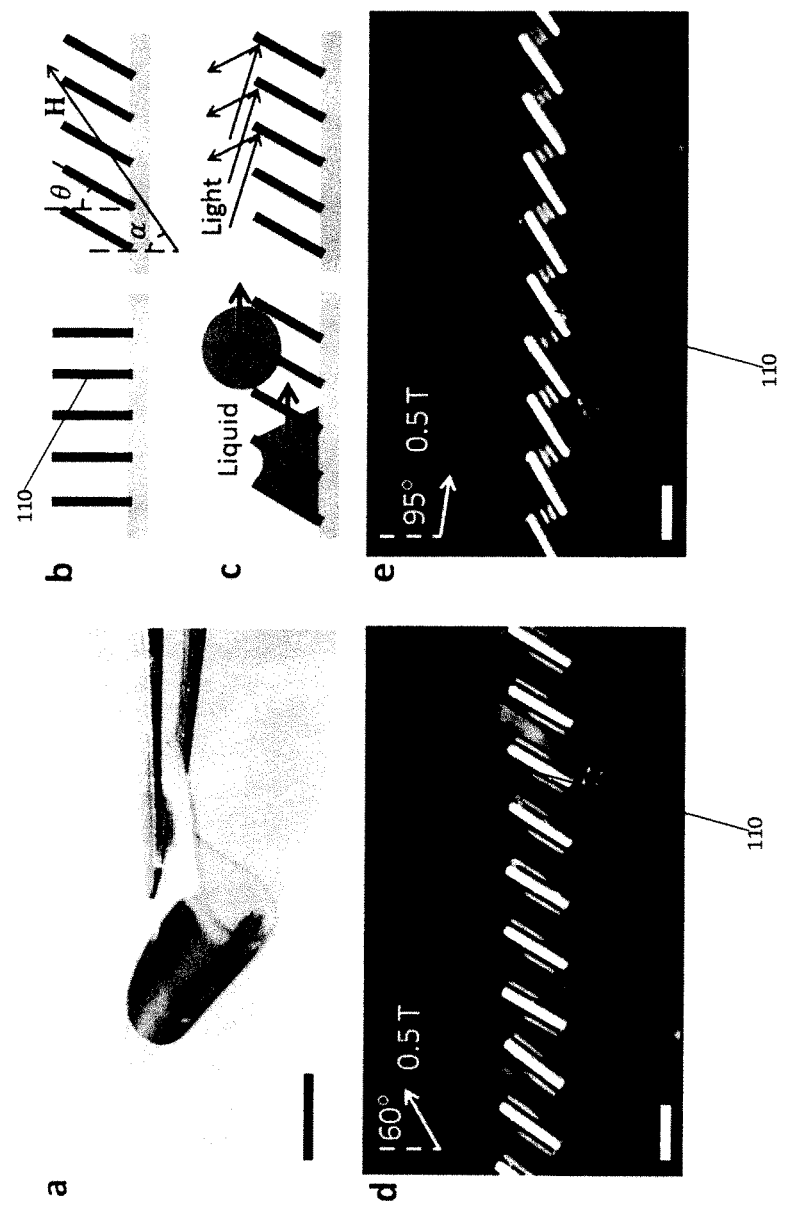
FIGS. 7(a)-7(e) depict a fabricated flexible uniform responsive microstructures (μFUR), a schematic showing the concept of μFUR where the tilt angle can be controlled via an external magnetic field, a schematic of potential applications including microfluidic and optical manipulation, a side view image of the fabricated μFUR with an applied magnetic field strength of 0.5 T and field angle of α=60°, and a side view image of the fabricated μFUR with an applied magnetic field strength of 0.5 T and field angle of α=95°, respectively, according to one embodiment.

FIGS. 1(a) and 7(b) each depicts the μFUR in scenarios in the absence of an applied magnetic field and with a magnetic field applied at a field angle that produces a tilt angle of the micropillars 110. As shown in FIGS. 1(b) and 7(c), the tilting of the micropillars 110 may be utilized to facilitate cell manipulation, droplet/bubble manipulation, directional liquid spreading and light interaction of the surface. According to one embodiment, the tunable surface may be incorporated in a tunable microfluidic device or in an a tunable optical device, or both.

A change in the tilt angle of the micropillars may produce a change in the properties of the μFUR. According to one embodiment the application of the magnetic field may produce a change in at least one of the surface drag, optical properties, spreading characteristics, wetting characteristics, heat transfer, surface adhesive properties, and audio characteristics of the μFUR. The application of the magnetic field may produce a uniform tilt angle of the micropillars. According to one embodiment, the application of the magnetic field may cause the at least some of the micropillars to contact one another.

NON-LIMITING WORKING EXAMPLES

Example 1

Figure 2:
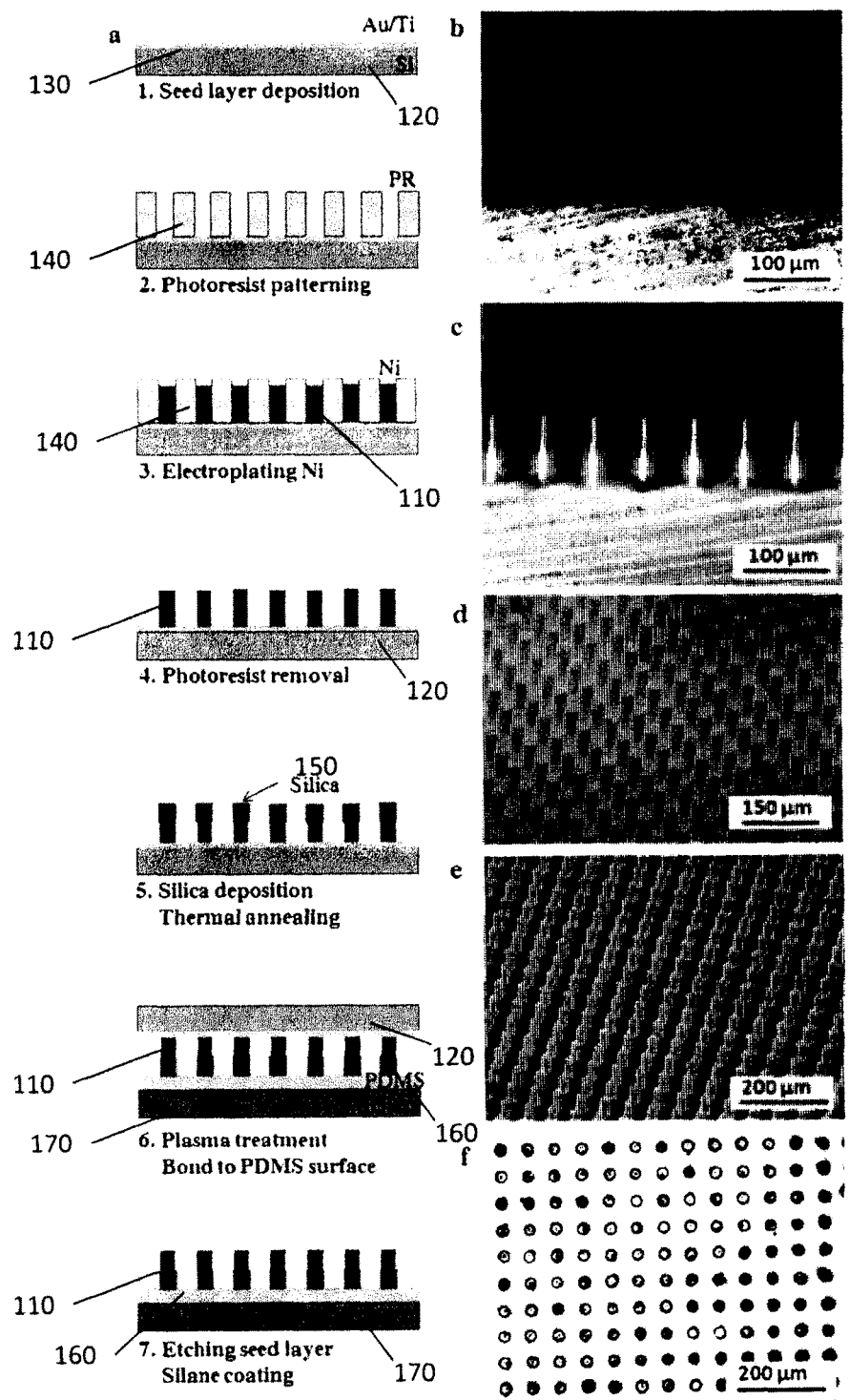
FIGS. 2(a)-2(f) depict a schematic of a fabrication process of magnetically tunable micropillar arrays, an optical microscope image of a sample after step 2, an optical microscope image after step 4, a scanning electron microscopy (SEM) image after step 4, an SEM image after step 7, and a top down optical microscope image of a sample after step 7, respectively, according to one embodiment.

Tunable surfaces including ferromagnetic micropillars with diameters of 24-27 μm, heights of 60-80 μm, and spacings of 60 μm resting on a soft PDMS substrate to achieve high tilt angles were produced. The magnetic micropillar arrays were fabricated by electroplating nickel, then bonding to a PDMS surface by a silica adhesion layer. FIG. 2(a) summarizes the fabrication process in this Example and the details are described as follows.

(1) Seed layer deposition: A 20 nm titanium layer was first deposited on a 6 inch silicon substrate by e-beam thermal evaporation as an adhesion layer, on top of which a 100 nm gold layer was deposited as the main seed layer. The Au/Ti seed layer 130 is schematically depicted on the silicon substrate 120 in FIG. 2(a).

(2) Photoresist patterning: A 100 μm thick negative photoresist 140 (KMPR 1050, MicroChem) layer was spin-coated on the seed layer 130 at 1300 rpm for 30 seconds, soft baked on a hotplate at 100° C. for 27 minutes, exposed to UV illumination at 750 mJ/cm$^2$, post baked at 100° C. for 6 minutes and developed inside a sonication bath for 15 min as shown in the optical microscope image of FIG. 2(b). The result was a thick photoresist layer 140 with uniform hole arrays. The wafer was then diced into 2×2 cm$^2$ samples.

(3) Electroplating nickel: To enhance the hydrophilicity of the photoresist mold surface, the sample was treated with oxygen plasma at 29 W/500 mTorr/30 minutes. The contact angle of the commercial nickel electroplating solution (Nickel Sulfamate RTU, Technic Inc.) on the photoresist patterned surface was reduced from 80° to 10° after the treatment, which allowed easy escape of bubbles produced inside the mold during electroplating. The sample was first sonicated in the electroplating solution for 45 seconds to remove air trapped in the hole arrays of photoresist. A dense array of nickel micropillars 110 was subsequently obtained by electroplating.

(4) Photoresist removal: The patterned photoresist surface was first softened and then lifted by immersing in acetone (room temperature, 8 hours) and in MicroChem Remover PG (70° C., 2 hours). Photoresist residue was oxidized by sodium permanganate and dissolved in methane sulfonic acid, leaving freestanding micropillars 110 on the substrate as shown in FIGS. 2(c) and 2(d), and optical microscope image and a SEM image, respectively.

(5) Silica deposition/thermal annealing: A 10 nm silica layer 150 was deposited on the micropillar 110 tips by plasma-enhanced chemical vapor deposition (PECVD). To enhance magnetic performance, the nickel micropillars were annealed at 300° C. under vacuum with an applied magnetic field of ~0.5 Tesla, perpendicular to the sample surface.

(6) Transferring to PDMS: A 70 μm PDMS layer 160 was spin-coated on a glass substrate 170, cured, and oxygen plasma treated (29 W/500 mTorr/10 minutes). The nickel micropillars 110 coated with silica 150 on the tips were subjected to the same plasma treatment condition and bonded to the PDMS 160 surface.

(7) Etching seed layer: The gold seed layer 130 was etched away by gold etchant (Sigma-Aldrich) such that the micropillars 110 (detached from the silicon substrate) remained only on the PDMS substrate 160 as shown in FIGS. 2(e) and 2(f).

Surfaces with uniform pillar arrays covering areas of 8 mm×8 mm were successfully produced, as shown in the SEM image in FIG. 2(e) and the top-down view optical microscope image in FIG. 2(f). The fabrication process is easily repeatable and scalable to even larger arrays.

After the photoresist removal (step 4), the magnetic properties of the micropillar arrays were characterized using vibrating sample magnetometry. It was confirmed that the micropillar arrays match the properties of bulk nickel with a coercivity of 60Oe and a magnetization saturation at a field strength of 0.3 Tesla, as shown in FIG. 3.

Figure 3:
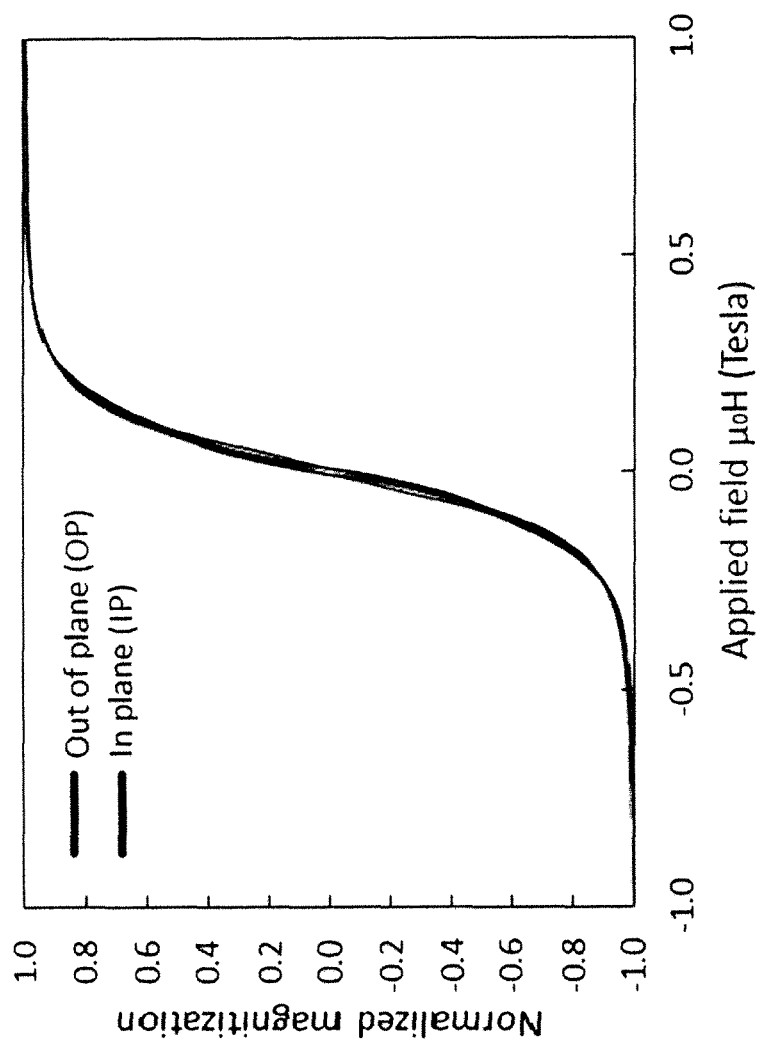
FIG. 3 depicts an in-plane and an out-of-plane magnetic hysteresis loop of electroplated nickel micropillar arrays on a silicon substrate, according to one embodiment.

The small hysteresis depicted in FIG. 3 indicates the magnetic softness of the electroplated nickel micropillar arrays on a silicon substrate. Even after annealing, the electroplated nickel material could be easily magnetized to saturation in the field direction, as well as de-magnetized after the field was removed. The magnetization direction of a soft magnetic material, however, depends on the constraints and applied field direction. The aspect ratio (~2.5) of the micropillars provided an easy-axis for the magnetization direction. Under no external constraints, the cylindrical nickel micropillars were preferentially magnetized in the micropillar axial direction, and the micropillars rotated to align with the field direction while maintaining the axial magnetization direction. However, since the micropillars were fixed on one end (standing on rigid silicon substrate), the magnetic microstructures were magnetized in the field direction regardless of its easy-axis direction, as indicated by the similarity of the measured hysteresis curves between the out-of-plane field direction and in-plane field direction shown in FIG. 3. In the case of a partially constrained pillar array, such as the sample after step 7, where pillars were constrained with one end on the soft PDMS substrate, but were allowed to tilt, when the pillars were first axially magnetized and subjected to changes in the field direction, the magnetization direction of the pillars followed the field direction, and decreased the angle between the magnetization of the pillars and the field. To generate a large magnetic torque to tilt the pillars, however, a large angle between the magnetization of the pillars and the field needs to be maintained. As a result, we realized dynamic tuning for our fabricated nickel microstructures by changing the field to keep a large angle between the magnetization of the pillars and the field.

Figure 4:
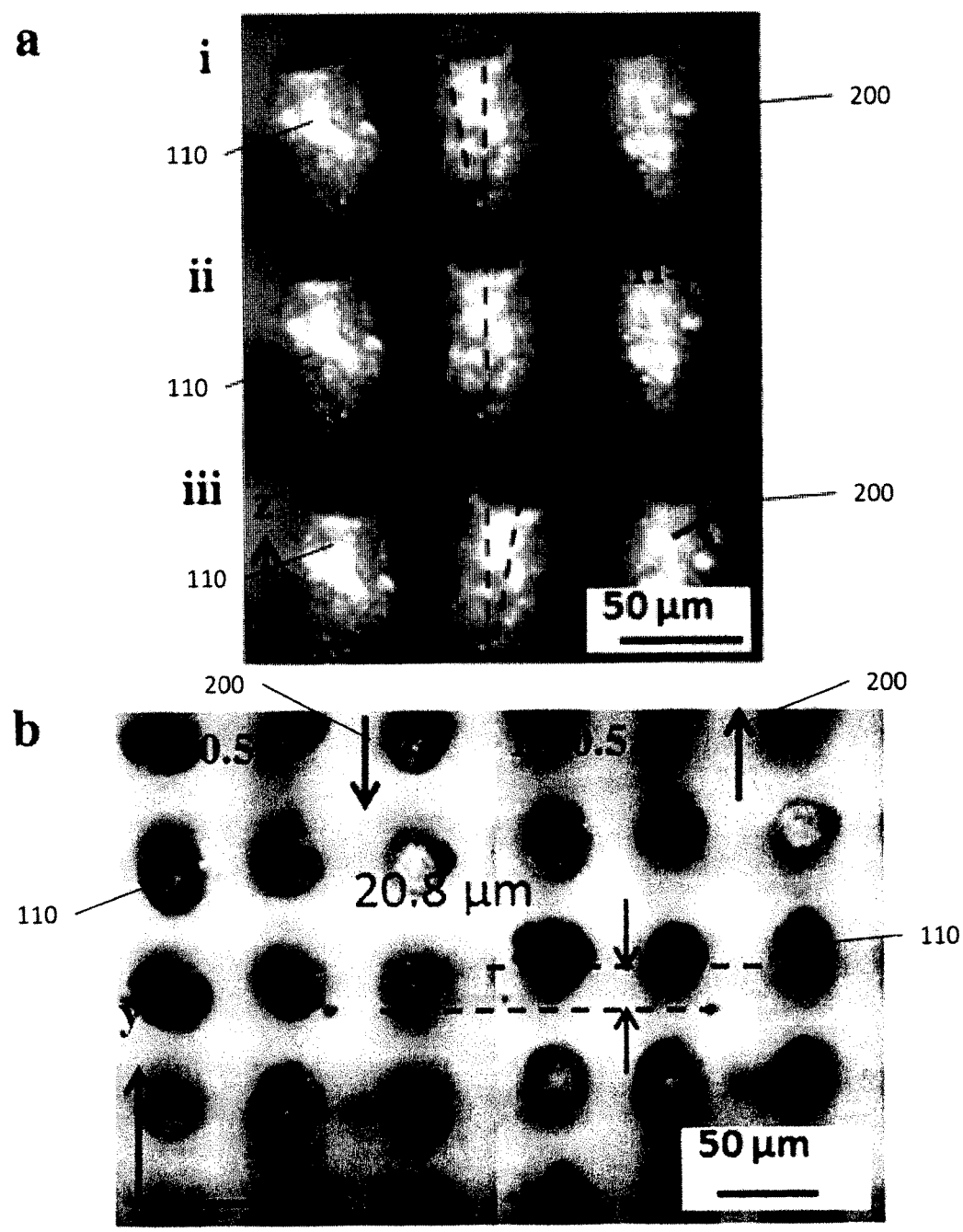
FIGS. 4(a) and 4(b) depict side view images of a tunable surface with a field strength of ~0.5 Tesla (T) and field angle varied from −60° to 60°, and top view images of a sample with a field strength of ~0.5 T and field angle varied from −60° to 60°, respectively, according to one embodiment.

The fabricated surfaces were characterized under an optical microscope. A 5597 Gauss axially magnetized neodymium disk magnet (D4H2, K&J Magnetics, Inc.) was first placed at a distance of 3 mm under the sample to introduce a magnetic field perpendicular to the sample surface. As a result, the micropillars were magnetized axially. After that, the disk magnet was repeatedly moved horizontally. Under these conditions, the maximum field strength and maximum field angle were estimated to be 0.5 Tesla and 60°, respectively. The micropillars 110 tilted uniformly with an average tilt angle of 10.5° as shown in FIG. 4(a) and FIG. 4(b), a side view and a top view, respectively. The direction of the field angle was varied from −60° to 60° from the normal to the surface as indicated by arrows 200 in FIGS. 4(a) and 4(b).

Figure 5:
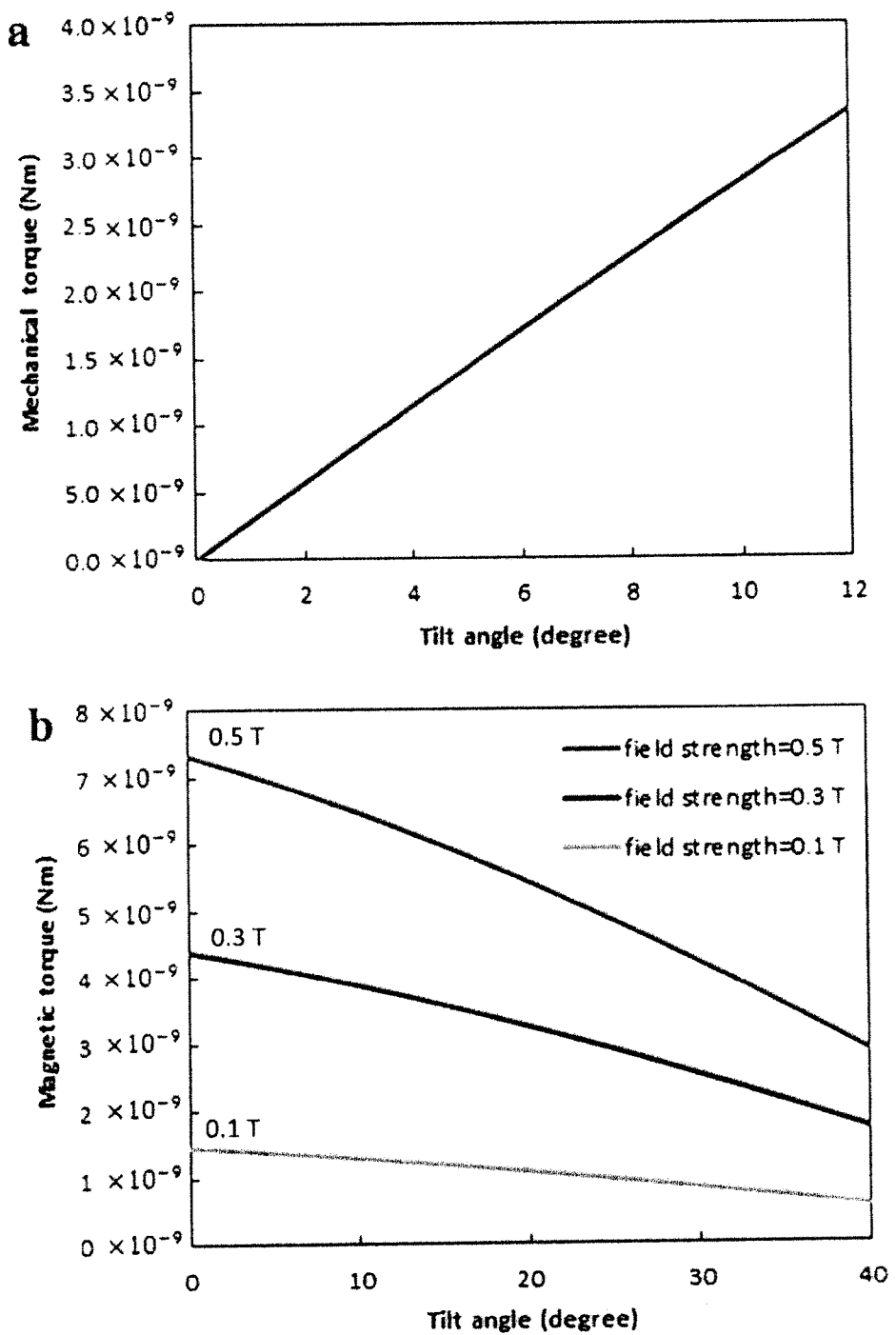
FIGS. 5(a) and 5(b) depict a finite element simulation (Abaqus) of tilt angle as a function of mechanical torque, and magnetic torque as a function of tilt angle for a variety of field strengths, respectively, according to one embodiment.

With the fabricated pillar geometry and magnetic properties, as well as the experimental configuration, finite element simulations were performed using Abaqus to determine the equilibrium position of the pillars under different mechanical torques $T_{mech}$. The model includes 80 μm nickel micropillars with 20 μm embedded into a layer of 100 μm soft PDMS, leaving 60 μm of the micropillars protruding above the layer. The micropillars in the model had a diameter of 26 μm. Multiple micropillars were considered in the model to represent periodic boundary conditions. The bottom surface of the PDMS layer was fixed while a mechanical torque was applied on each of the pillars in a clockwise direction. The tilt angle was obtained at an equilibrium position with an applied mechanical torque as shown in FIG. 5(a).

The magnetic torque was calculated by equation (1), $$T_{mag} = V\vec{M} \times \vec{B} \quad (1)$$

where V is the volume of the magnetic micropillar, $\vec{M}$ is the magnetization of cylindrical microstructures and is assumed to be in axial direction, and $\vec{B}$ is the magnetic flux density. Considering the micropillar geometry, applied field strength and field angle, equation (1) was rearranged, $$T_{mag} = \frac{\pi}{4} d^2 h M \mu_0 H \sin(\alpha - \theta), \quad (2)$$

where d and h are respectively the diameter and height of the micropillars, M is the magnitude of magnetization, $\mu_0$ is the vacuum permeability, H is the magnitude of the applied field, α is the field angle defined as the angle between applied field and surface vertical direction, and θ is the pillar tilt angle. The magnetic torque is shown in FIG. 5(b) for a filed angle of 60°.

Figure 6:
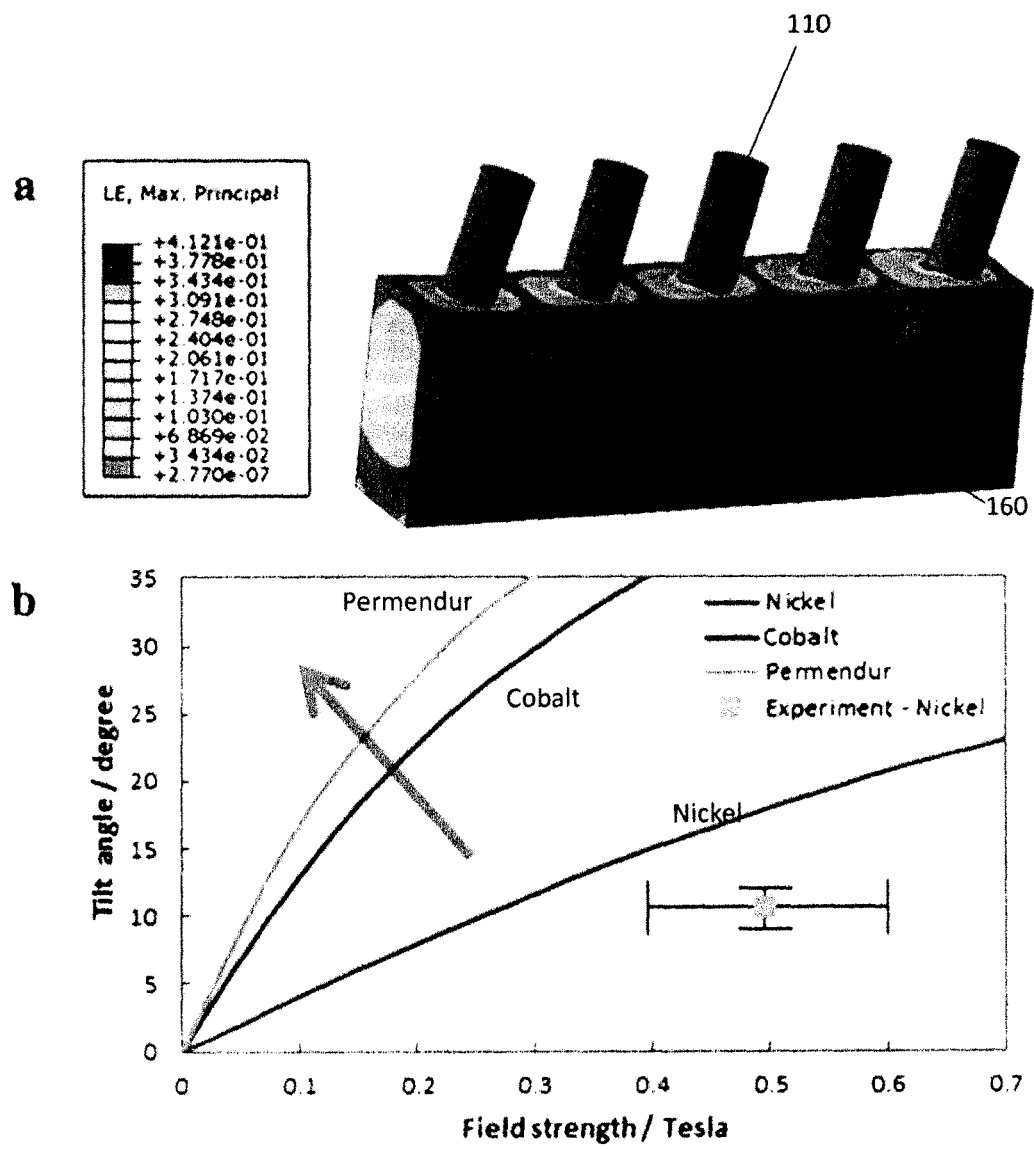
FIGS. 6(a) and 6(b) depict a graphical representation of a finite element simulation of tilt angle of a micropillar array under a mechanical torque, and a simulation result of tilt angle as a function of field strength for a variety of different magnetic materials and the experimental result of fabricated nickel pillars, respectively, according to one embodiment.

At equilibrium, the magnetic torque exerted on a single pillar should equal the mechanical torque needed to tilt the pillar. As an example, a 20° tilt angle was predicted with a torque generated by a magnetic field strength of 0.7 Tesla at a 60° field angle as depicted in FIG. 6(a). The legend in FIG. 6(a) represents the logarithmic principle strain. By combining the simulation results with the magnetic torque calculation, the equilibrium tilt angle for a field angle of 60° with different magnetic materials was obtained as shown in FIG. 6(b). The experimental results show reasonable agreement with the model, however the uncertainty in the Young's modulus of the fabricated PDMS layer, as well as the field strength and angle at the sample surface, the existence of a non-magnetic oxide layer on nickel micropillars, and the magnetic softness of the nickel material may have led to the discrepancy in results.

The effect of different magnetic materials was also investigated to broaden the applicability of the fabrication method. FIG. 6(b) shows that by changing the magnetic material from nickel to cobalt or permendur (50% cobalt and 50% nickel), the tilt angle may be increased while decreasing the associated magnetic field strength significantly. Thus, other ferromagnetic materials may be utilized to form the micropillars and achieve different magnetic properties, as shown in FIG. 6(b), for magnetically tunable arrays.

The produced magnetically tunable surfaces allow the tilt angle of the micropillar arrays to be controlled by an external magnetic field. An 8 mm×8 mm surface with uniform electroplated nickel micropillar arrays bonded on a PDMS substrate was successfully fabricated. A field strength of 0.5 Tesla and a field angle of 60° produced a uniform tilt angle of the micropillar arrays of 10.5°. The produced tunable surface designs can serve as important device platforms in microfluidics, biological and optical applications—such as actively transporting water droplets or spreading a liquid film by micropillar movement.

Example 2

Figure 8:
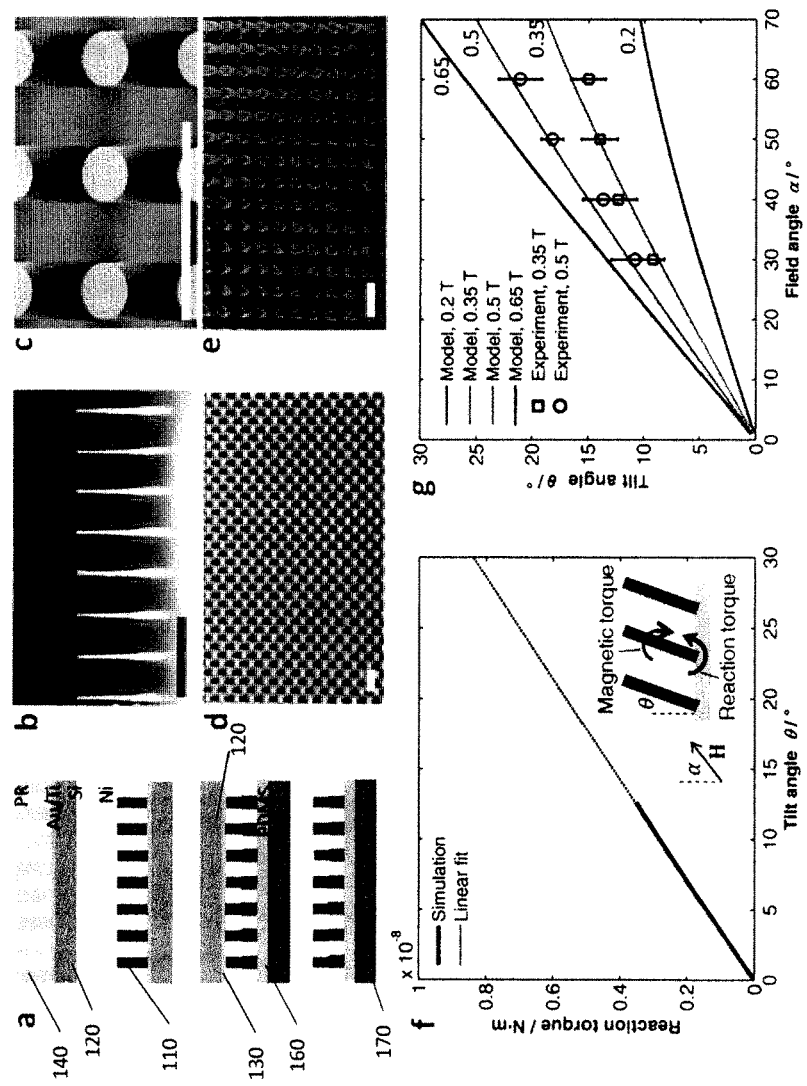
FIGS. 8(a)-8(g) depict a schematic representation of a fabrication process, an optical microscope image of a nickel pillar array on silicon, an SEM image of a nickel pillar array on silicon, an SEM image of a nickel pillar array on silicon, an SEM image of a nickel pillar array bonded to PDMS, a finite element simulation (Abaqus) of the reaction torque as a function of the tilt angle, and a calculation and experimental results of tilt angle as a function of field strength and field angle, respectively, according to one embodiment.

The flexible uniform responsive microstructures (μFUR) were created by fabricating ferromagnetic micropillars and then bonding to a soft PDMS substrate. A μFUR is shown in FIG. 7(a) wherein the dark portion is the micropillar array and the transparent portion is the PDMS elastic layer. A dense array of nickel pillars as shown in FIGS. 8(b)-8(d), with diameters (d) of 26-30 μm, heights (h) of 70-75 μm, and spacings (l) of 60 μm, was electroplated. The geometries were chosen in this Example due to the ease of fabrication. The nickel posts were subsequently bonded to a PDMS surface through a silica adhesion layer FIG. 8(e). The scale bars in the SEM image of FIG. 8(e) are 100 μm. The fabrication of μFUR was demonstrated repeatably over an area of 8 mm×8 mm and can be easily scaled to larger arrays.

The μFUR was fabricated by a multi-step process as depicted in FIG. 8(a). First, a photoresist 140 was patterned on a gold (Au) seed layer and a titanium (Ti) adhesion layer 130 e-beam evaporated on a silicon (Si) substrate 120. Second, nickel (Ni) was electroplated inside the photoresist mold and then the photoresist was stripped. Third, the nickel micropillars 110 were bonded to PDMS 160 through a silica adhesion layer 150. Finally, the silicon substrate 120 was detached from the micropillars 110.

With the fabricated micropillar geometry and magnetic properties, a computer simulation model was developed to predict the equilibrium micropillar tilt angle θ under various magnetic field conditions. The model was based on the balance of a magnetic torque generated by an external magnetic field and a corresponding reaction torque from the constraint of the PDMS substrate, as shown in the inset of FIG. 8(f). The reaction torque was obtained from finite element simulations utilizing Abaqus, which indicated a linear relation between the reaction torque and the micropillar tilt angle θ as shown in FIG. 8(f) for micropillars with a height of 80 μm and a diameter of 26 μm. FIG. 8(g) shows that θ increased with both the magnetic field strength and field angle α. To measure the tilt angle of the fabricated μFUR, a magnetic field was applied using two parallel neodymium disc magnets. The magnetic field strength and field angle were determined by the orientation, diameter, thickness and spacing of the magnets. The experimental data shown in FIG. 8(g) were taken when the magnetic field was kept at constant strength and field angles. The error bars in FIG. 8(g) account for the standard deviation of measurements on 30 micropillars and an estimated system error. The equilibrium tilt angle θ was obtained by side view microscope images of the pillar arrays as shown in FIGS. 7(d) and 7(e) for a field strength of 0.5 T and field angles of 60° and 95°, respectively. The scale bars in FIGS. 7(d) and 7(e) are 50 μm. The tilt angle response of the micropillars to a field angle change was instantaneous and no apparent hysteresis was observed over multiple measurement cycles due to the small hysteresis in the magnetization shown in FIG. 10. The experimental results are in excellent agreement with the model as shown in FIG. 8(g), which demonstrates the ability to accurately control the micropillar tilt angle with an external field.

Figure 9:
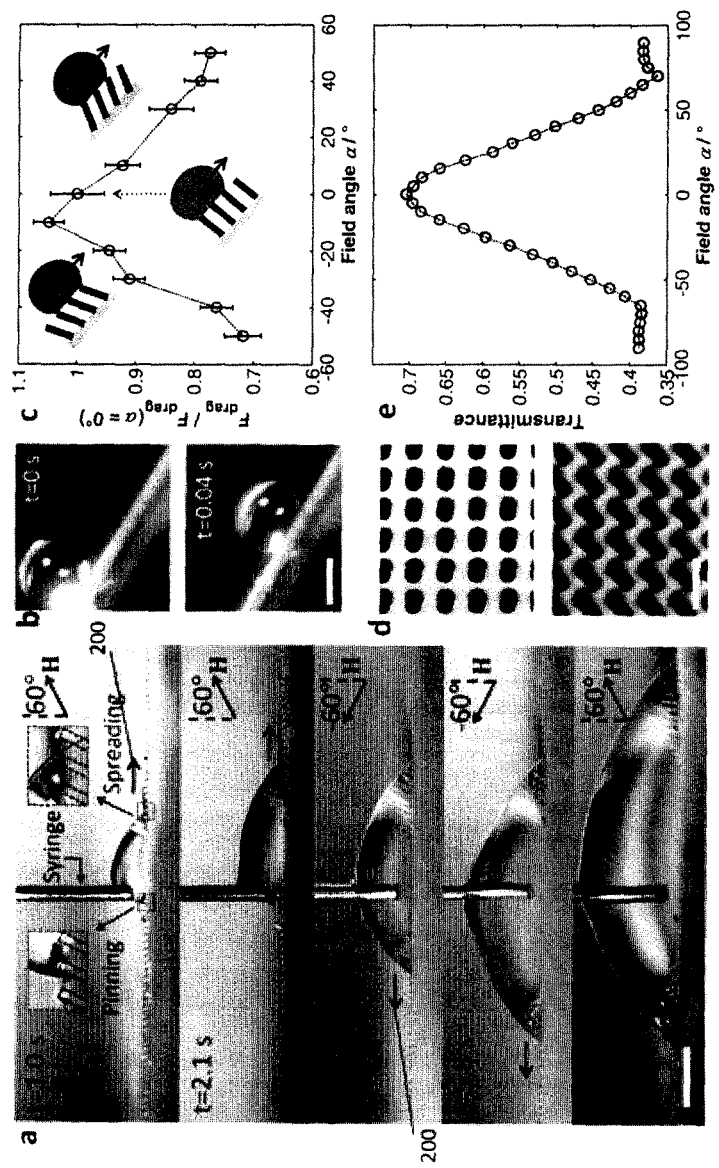
FIGS. 9(a)-9(e) depict a fluid spreading direction dynamically controlled while the fluid only propagates in the pillar tilt direction produced by an external magnetic field and is pinned in all other directions, time-lapse images of a water droplet sliding on a μFUR, a normalized drag force as a function of the field angle in a field strength of 0.35 T, top view images of the tunable surface with field angles of 5° and 70°, and the transmittance of a 635 nm laser as a function of the magnetic field angle of a μFUR, respectively, according to one embodiment.

The versatility of the μFUR to dynamically manipulate liquid spreading, control fluid drag and tune optical transmittance was tested. First, real-time liquid directional spreading by dynamically changing the pillar tilt orientation and angle was demonstrated, where past studies have only shown uni-directional wetting in a fixed direction on static asymmetric structures. A wetting liquid (30% IPA and 70% water) was introduced to the surface, which satisfies the imbibition condition to the surface, through a syringe at a constant flow rate of 0.25 μL s$^{-1}$ as shown in FIG. 9(a). The liquid film propagated only if the contact line was able to reach the next row of the micropillars as depicted in the inset of FIG. 9(a). The figure tilt direction is indicated by arrows 210 in FIG. 9(a), and the scale bar is 0.5 mm. The surface was initially subjected to a magnetic field tilted to the right (α=60°, μ$_0$H=0.5 T) and the fluid only flowed in the pillar tilt direction while being highly pinned in all other directions. At t=2.5 s and t=6.2 s, the direction of the magnetic field was switched. As a result, the fluid instantaneously changed its propagating and pinning directions. This dynamic manipulation may be achieved when the pillar tilt angle θ is above 12° for 30% IPA and 70% water, which is in agreement with a model developed for static asymmetric structures. Furthermore, this repeatable and instantaneous manipulation capability is not restricted to the ±x direction, but can be applied to all directions on the 2D surface, and even on a vertically inclined surface.

Figure 13:
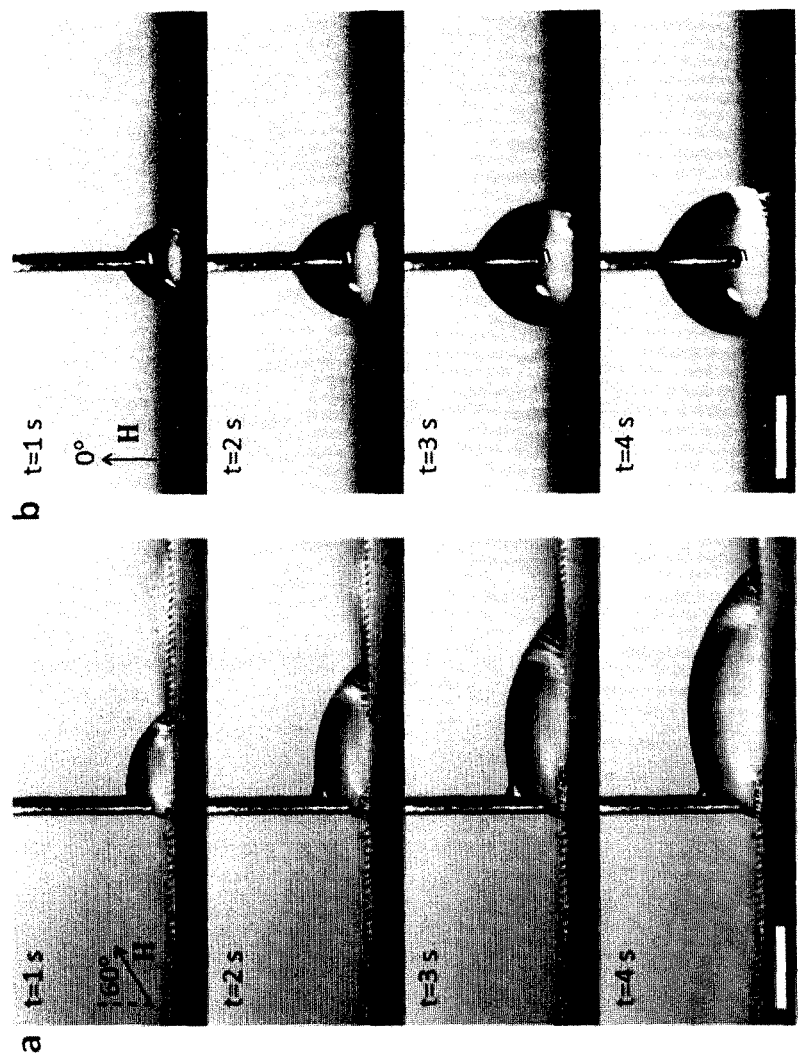
FIGS. 13(a) and 13(b) depict a fluid spreading on μFUR under a magnetic field angle of 60° and a magnetic field angle of 0°, respectively, according to one embodiment.

Under the magnetic field, the asymmetric structures may initiate a preferential propagation direction as of a fluid, which is determined by the micropillar tilt angle, spacing and the intrinsic contact angle of the liquid on the surface. As shown in FIG. 13(a) a fluid spreads preferentially on the μFUR to the right under the influence of a magnetic field angle of 60° and a field strength of 0.5 T while being pinned in all other directions. By contrast, FIG. 13(b) demonstrates that when the magnetic field angle is 0° with a field strength of 0.5 T the fluid spreads equally in all directions. The scale bar in each of FIGS. 13(a) and 13(b) is 0.5 mm.

The μFUR may also be employed to tune the drag force with high surface tension fluids, e.g., water. By increasing the tilt angle of the μFUR the effective fluid-surface contact area (solid fraction) decreases, and changes the fluid-solid interface morphology. The sliding behavior of a water droplet (7 μL) on a tilted surface was examined under various field angles at 0.35 T as shown in FIG. 9(b), the velocity and acceleration of which were extracted from the time-lapse images captured by a high-speed camera to obtain the drag force. The scale bar in FIG. 9(b) is 2 mm.

Figure 14:
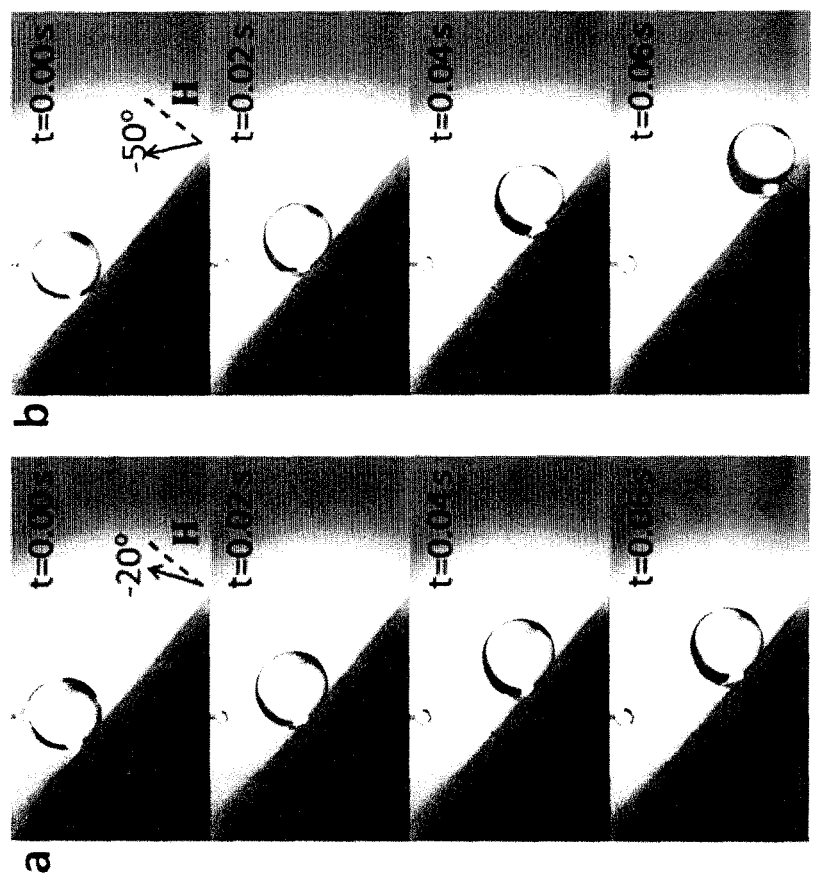
FIGS. 14(a) and 14(b) depict time-lapse high-speed camera images of a water droplet sliding on a μFUR tilted at 40° under a magnetic field of 0.35 T at a magnetic field angle of −20° and a magnetic field angle of −50°, respectively, according to one embodiment.

The displacement data, e.g., in FIG. 14, indicates that the droplet experiences a short acceleration period after detaching from the needle, and then transitions to a steady deceleration mode due to the drag force. The acceleration originates from the deformation of the droplet shape which lowers its potential energy and converts it to kinetic energy. A second order polynomial relation between the displacement x and time t was observed for the deceleration mode (t>0.014 s), indicating a constant drag force for each situation, i.e., α=d$^2$x/dt$^2$. The drag force, F$_{drag}$, was then determined based on a force balance, $$ma = mg \sin(\beta) - F_{drag} \quad (3)$$

where β is the slope angle (40°) and m is the mass of the droplet. The drag force was normalized with respect to the zero field angle case (α=0°) to facilitate a comparison. A maximum reduction in drag of 28% for a field strength of 0.35 T was observed at a field angle of -50° as shown in FIG. 9(c), with the negative field angle indicating that the angle is against the sliding direction. The maximum value of drag force at α=-10° shows no statistically significant difference when compared with the value at α=0° (within the error bars). The drag force decreases with an increase in tilt angle both against the flow and with the flow due to the effect of reduced solid fraction.

Figure 16:
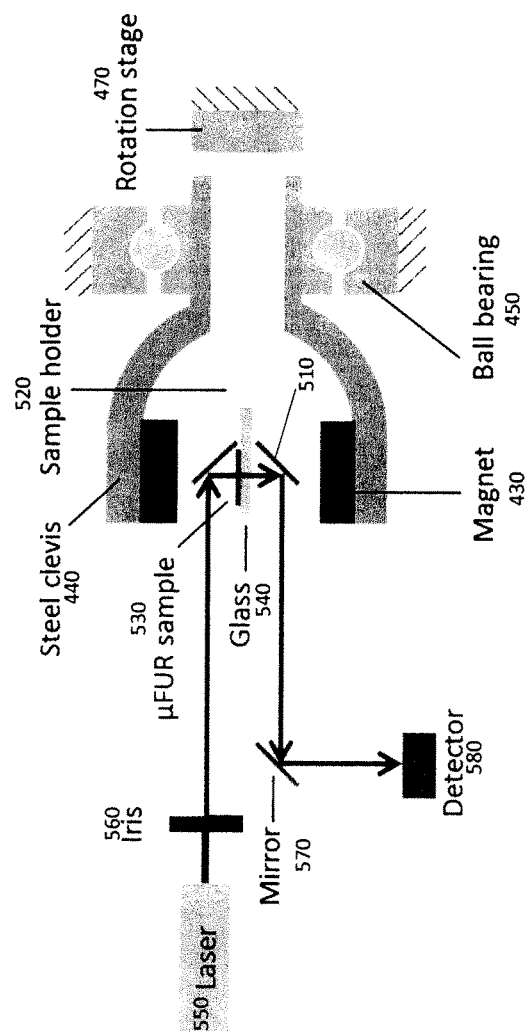
FIG. 16 depicts a schematic of a transmittance measurement system, according to one embodiment.

The difference in the optical properties between the opaque pillar surface and the transparent PDMS film provides additional opportunities for dynamic optical tuning. This is typically difficult to achieve using hydrogel structures or PDMS structures mixed with magnetic particles because the refractive indices of the hydrogel and the surrounding liquid are similar, and both the substrate and the micropillars of PDMS/magnetic particle composite mixtures have the same optical properties. It was demonstrated that by utilizing the asymmetry of the microstructures as shown in FIG. 9(d), the surface can function similarly to "window blinds." where the transmittance can be tuned on demand. The images in FIG. 9(d) are top view images of the tunable surface under magnetic field angles of 5° and 70°, with the scale bar being 100 μm. The transmitted power of a collimated laser beam (λ=635 nm, spot size was 1.5-2 mm) was measured through the sample using a photodiode detector as shown in FIG. 16. The transmittance of μFUR was calculated using the detected power of the laser beam through the sample and the glass normalized by the detected power through the glass only. Transmittance of the μFUR ranging from 0.38 to 0.71 under different magnetic field angles at 0.35 T was observed as shown in FIG. 9(e). The response was instantaneous and the results were repeatable.

A tunable and controlable platform using a simple fabrication approach, which has a large tuning range (0-57° tilt angles) with precise and continuous control, was demonstrated. The versatile μFUR is capable of dynamic manipulation of fluid spreading directionality, fluid drag, and can tune optical transmittance over a large range by adjusting the applied magnetic field. The experimental results indicate opportunities for real-time fluid and light manipulation. Biomimetic functionalities such as locomotion and liquid or cell transport may be achieved by applying localized and variable magnetic fields. The size of the micropillars may be scaled down to the order of the wavelength of visible light, such that the structures can coherently manipulate light propagation and act as tunable photonic crystals. By tuning the geometry, wettability, optical properties and surface chemistry of the micropillars and the substrate, the surface can expand its manipulation capabilities, and serve as an important platform for applications such as smart windows, versatile artificial skin, cell manipulation, dynamic optical devices and fluid control.

Figure 12:
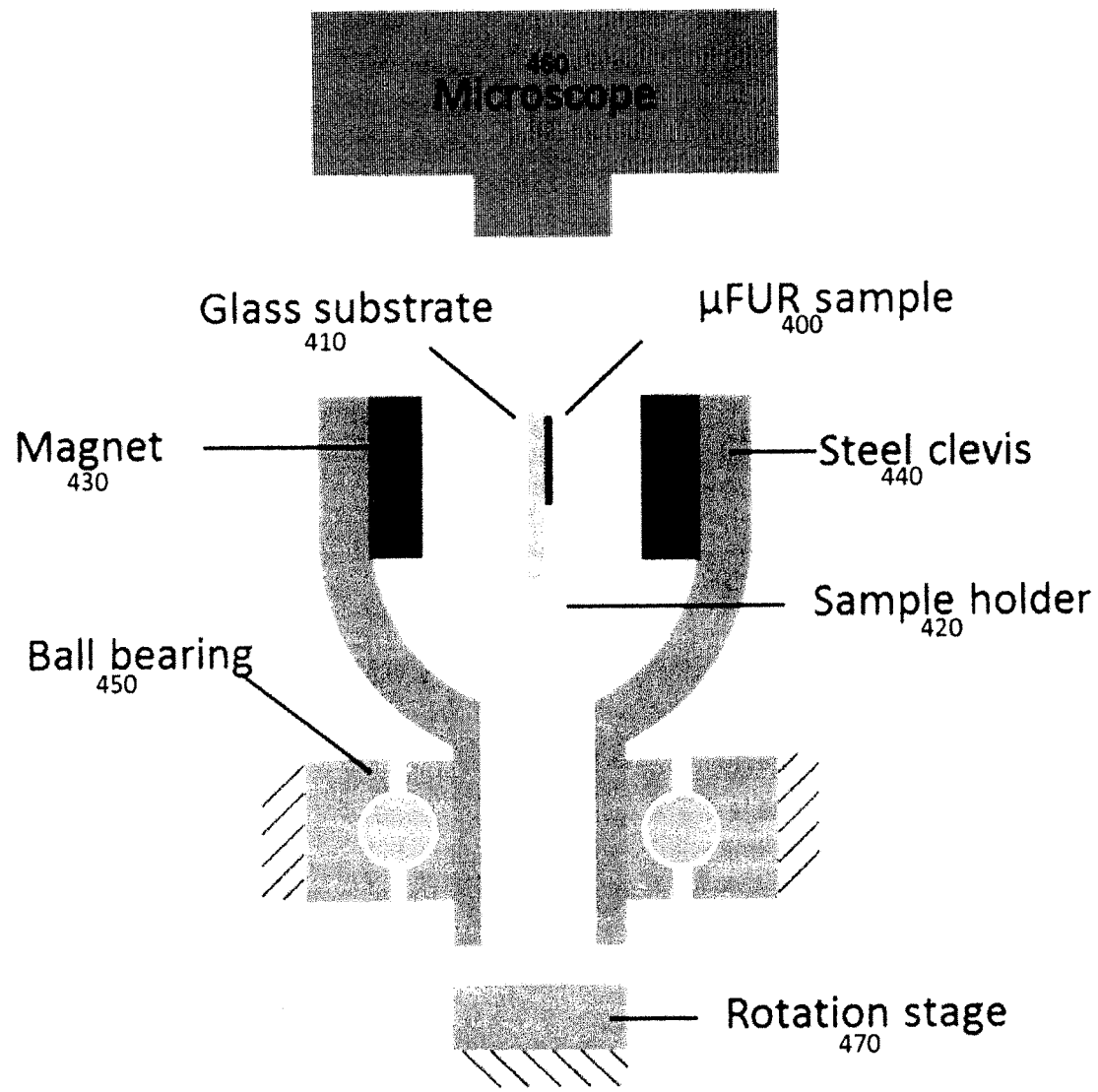
FIG. 12 depicts a schematic of a tilt angle measurement system according to one embodiment.

The experimental setup to measure the tilt angle is illustrated in FIG. 12. An optical microscope 460 was used to capture the side view images of the pillar arrays. The µFUR sample 400 is attached to a glass slide 410, which is inserted into a cylindrical Teflon sample holder 420. To provide an external magnetic field, the sample was placed between two neodymium disc magnets 430 (Grade N52, K&J Magnetics, Inc.) which were placed parallel to each other on the two arms of a steel clevis 440. The clevis was inserted into a ball bearing support 450 so that the attached magnets 430 could be rotated around the sample surface by a rotation stage 470 while maintaining a constant field strength during rotation. The magnetic field orientation was controlled by rotating the clevis, and the magnetic field strength was calculated by K&J Magnetics Gap Calculator (K&J Magnetics) based on the diameter, thickness and gap. Tilt angles in magnetic fields of 0.35 T and 0.5 T were measured as a function of field angles.

To measure the drag force, the sliding behavior of a water drop (7 µL) on a tilted µFUR surface (40°) under various field angles and a field strength of 0.35 T was examined. The initial condition was kept the same for all of the experiments. DI water supplied by a syringe at a fixed flow rate of approximately 2.5 µL s$^{-1}$ was used as the test fluid. The distance between the syringe needle and the tunable surface was adjusted such that the droplet just touched the surface when it detached from the needle. High-speed camera imaging (Phantom v7.1, Vision Research) at 500 frames s$^{-1}$ was used to capture the droplet displacement x as a function of time t as shown in FIGS. 14(a) and 14(b), and reported in FIGS. 15(a) and 15(b), for magnetic field angles of −20° and −50°, respectively. The scale bars in FIGS. 14(a) and 14(b) are 2 mm.

The experimental setup utilized to measure transmittance is illustrated in FIG. 16. Two mirrors 510 at an angle of 90° were attached to the sample holder 520 with one 45° above the horizontal and the other 45° below the horizontal. The tunable surface sample 530 was placed on a horizontal glass slide 540 between the two mirrors. A laser 550 with a 635 nm wavelength (LTG6351AH, Lasermate Group, Inc.) was used as the light source for the measurement. The laser had an elliptical beam profile (3.3 mm×3.6 mm), and was well-collimated with a beam divergence of less than 0.5 mrad. An iris 560 (ID-1.0, Newport) was used to define a circular spot shape of the laser beam. The beam diameter of the laser 550 after the iris 560 was 1.5-2 mm. The laser 550 was adjusted such that the beam was horizontal and transmitted through the tunable surface 530 as indicated by FIG. 16. The distance between the laser source and the sample was approximately 13 cm. A third mirror 570 was used to reflect the transmitted laser beam to a photodiode detector 580 (818UV, Newport) connected to a power meter (1918C, Newport). The transmittance of µFUR was calculated using the detected power of the laser beam through the sample 530 and the glass substrate 540 normalized by the transmittance through the glass only. The measured transmittance through the fabricated PDMS substrate was 0.91±0.03. The magnet setup was the same as depicted in FIG. 12.

Example 3

A flexible uniform responsive microstructure (µFUR) was produced. A 100 nm gold layer was deposited on top of a 20 nm titanium adhesion layer as the main seed layer on a 6 inch silicon substrate by e-beam thermal evaporation. A 100 µm thick negative photoresist (KMPR 1050, MicroChem) layer was spin-coated on the seed layer at 1300 rpm for 30 s, soft baked on a hotplate at 100° C. for 27 min, exposed to UV illumination at 750 mJ cm$^{-2}$, post baked at 100° C. for 6 min and developed for 15 min. The result was a thick photoresist layer with uniform hole arrays. The wafer was then diced into 2×2 cm$^2$ samples. To remove air trapped in the hole arrays of the photoresist, the sample was treated with oxygen plasma (29 W at 500 mTorr for 30 min) and sonicated in the plating solution for 45 s. A dense array of nickel micropillars was subsequently obtained by electroplating (Nickel Sulfamate RTU, Technic Inc.) at 50° C. for 6 hours with a current density of 13 mA cm$^{-2}$. The patterned photoresist surface was lifted by immersing in acetone (room temperature, 8 hours) and in MicroChem Remover PG (70° C., 2 hours). Photoresist residue was oxidized by sodium permanganate and dissolved in methane sulfonic acid. The sample was rinsed with DI water. A ~10 nm silica layer was deposited on the pillar tips by plasma-enhanced chemical vapor deposition (PECVD). A 100 µm PDMS layer was spin-coated on a glass substrate, cured, and oxygen plasma treated (29 W at 500 mTorr for 10 min). The nickel pillars coated with silica on the tips were subjected to the same plasma treatment conditions and bonded onto the PDMS surface. The sample was immersed in a nickel compatible gold etchant (Sigma-Aldrich) and degased. The solution was then heated to 70° C. on a hotplate for 2 hours to etch away the gold seed layer such that the pillars (detached from the silicon substrate) remained only on the PDMS substrate.

Figure 10:
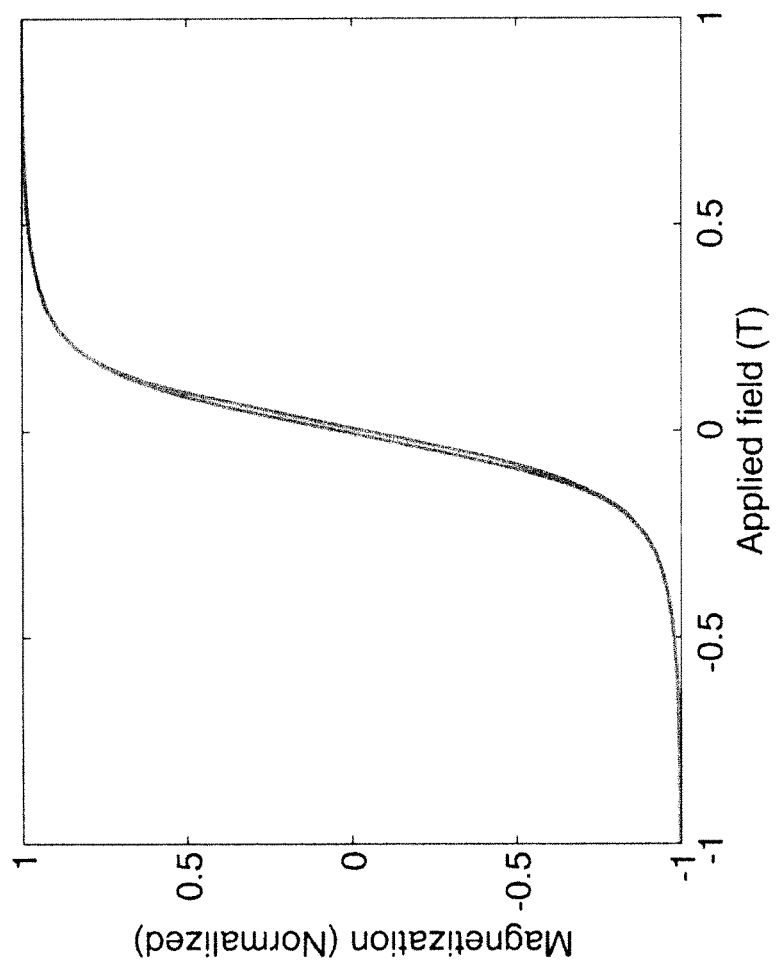
FIG. 10 depicts a normalized magnetization of the electroplated nickel micropillar arrays as a function of applied magnetic field measured by vibrating sample magnetometer, according to one embodiment.

After the photoresist removal, the magnetic properties of the pillar arrays were characterized using vibrating sample magnetometer (VSM), and confirmed that they match the properties of bulk nickel with a coercivity of 60oe (4.8×10$^3$ A m$^{-1}$). The measured magnetization M was normalized with respect to the saturation value ($M_{sat}$=0.6 T for nickel). Magnetization saturation at an applied magnetic field strength of 0.3 T is shown in FIG. 10. The measured magnetization was used in the model to calculate the magnetic torque and to calculate the tilt angle θ.

A model consisting of 80 µm nickel micropillars attached to a layer of 100 µm soft PDMS with the fabricated pillar geometry and magnetic properties, where the bottom surface of the PDMS layer was fixed was considered. The magnetic torque is given by Equation 4, $$T_{mag} = VM \times B \quad (4)$$

where V is the volume of the magnetic micropillar, M is the magnetization of the nickel micropillars which is assumed to be in the axial direction, and B is the magnetic flux density.

Figure 11:
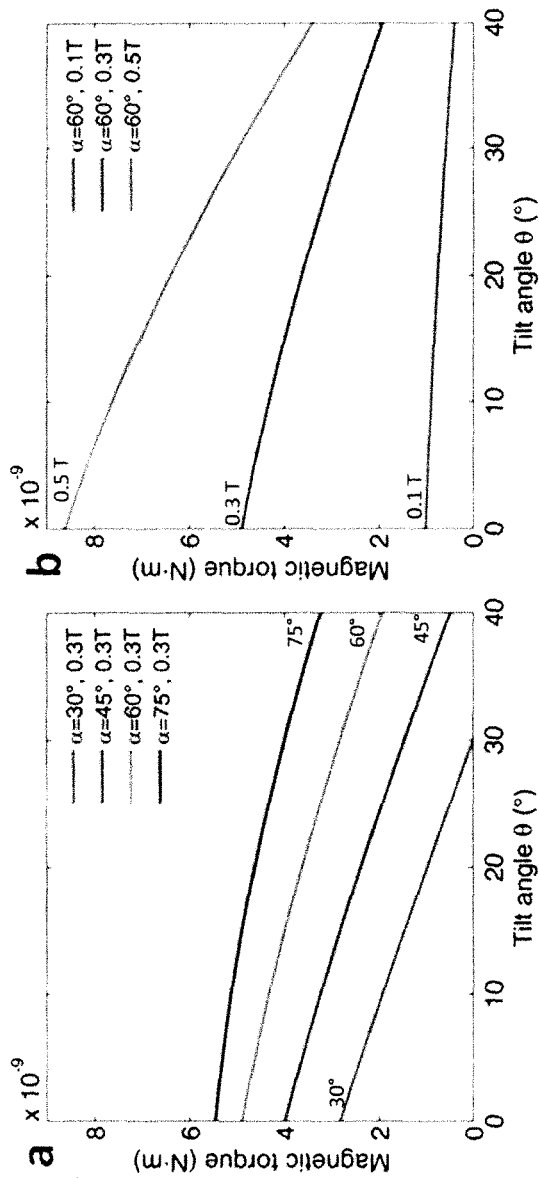
FIGS. 11(a) and 11(b) depict magnetic torque as a function of tilt angle under different magnetic field angles and field strength, respectively, according to one embodiment.

Considering the pillar geometry, applied field strength and field angle, the magnetic torque was calculated as, $$T_{mag} = \frac{\pi}{4} d^2 h M \mu_0 H \sin(\alpha - \theta), \quad (5)$$

where d and h are the diameter and height of the pillars, M is the magnitude of magnetization, $\mu_0$ is the vacuum permeability, H is the magnitude of the applied field, α is the field angle defined as the angle between the applied field and the surface vertical direction, and θ is the pillar tilt angle. FIGS. 11(a) and 11(b) show the magnetic torque as a function of the tilt angle θ for different magnetic field angles and field strengths, respectively, according to Equation 5. $T_{mag}$ increases with both the magnetic field angle and field strength.

The relationship between the reaction torque and the tilt angle was obtained using finite element simulations (Abaqus). The model consists of a 100 µm thick PDMS substrate with the bottom surface fixed. Five pillars were built in the model and the periodic boundary conditions were assumed valid for the pillar in the center. The nickel pillars (heights h=80 µm, diameters d=26 µm, spacings l=60 µm) were adhered to the PDMS layer with 60 µm above the PDMS surface and 20 µm embedded in the PDMS layer. Contact surfaces between the PDMS and the pillars were tied together. A torque was applied on each micropillar (clockwise). All other surfaces were free surfaces. An equilibrium tilt angle of the pillar in the center was captured by the model under each applied torque ranging from 0 N·m to 3.5×10$^{-9}$N·m as shown in FIG. 8(f). FIG. 6(a) shows an example of the model when the applied torque is 3.5× 10$^{-9}$N·m. The reaction torque $T_{reaction}$ from the PDMS has the same magnitude as the applied torque at equilibrium.

The tilt angle θ of the micropillars under an applied magnetic field was calculated by solving Equation 6, which is a torque balance equation between the magnetic torque and the reaction torque.

$$T_{mag}(\theta, H, \alpha) = T_{rection}(\theta) \quad (6)$$

The final result was expressed as θ=f(H, α) as shown in FIG. 8(g).

Figure 15:
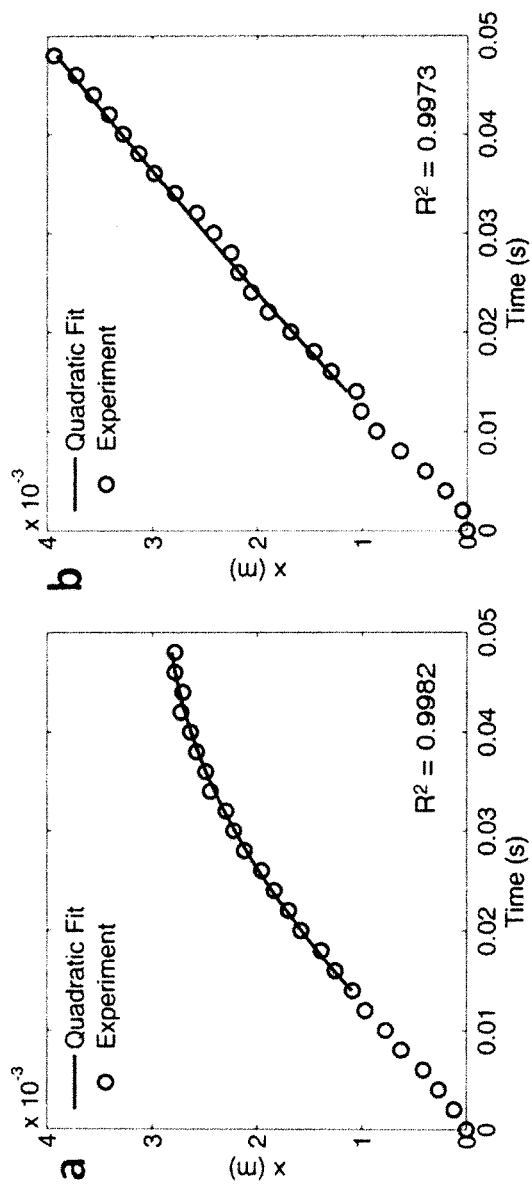
FIGS. 15(a) and 15(b) depict water droplet sliding displacement x as a function of time on a tunable surface with a 0.35 T magnetic field and field angles of α=−20° and α=−50°, respectively, according to one embodiment.

To compare the effect of the magnetic field angle α on the drag force, $F_{drag}$ wsa normalized as shown in Equation 7, $$\frac{F_{drag}(\alpha)}{F_{drag}(\alpha = 0°)} = \frac{g\sin(\beta) - a(\alpha)}{g\sin(\beta) - a(\alpha = 0°)}, \quad (7)$$

where β is the slope angle. FIGS. 15(a) and 15(b) show a higher deceleration at α=-20°, FIG. 15(a), than α=-50°, FIG. 15(b), indicating a higher drag force at α=-20°. When α=-50°, the displacement is approximately linear with time, indicating a reduced drag force close to mg·sin(β).

Additional Notes

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of" and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed:

1. A structure comprising:
an elastic layer, and
a plurality of ferromagnetic micropillars disposed over the elastic layer,
wherein the elastic layer has an elasticity that is greater than an elasticity of the micropillars.

2. The structure of claim 1, wherein the micropillars comprise at least one of nickel, cobalt and iron.

3. The structure of claim 1, wherein the micropillars have at least one of
a diameter of less than or equal to about 100 microns, and
a height of less than or equal to about 100 microns.

4. The structure of claim 1, wherein the micropillars have an aspect ratio of at least about 2.

5. The structure of claim 1, wherein the micropillars are cylindrical.

6. The structure of claim 1, wherein the micropillars are arranged in a periodic array.

7. The structure of claim 1, wherein the micropillars have a homogeneous composition.

8. The structure of claim 1, wherein the elastic layer comprises a polymer.

9. The structure of claim 1, wherein the elastic layer comprises PDMS.

10. A method of producing a structure comprising:
patterning a photoresist disposed over a substrate to form a template,
disposing a ferromagnetic material over the substrate to form micropillars comprising the ferromagnetic material,
removing the photoresist,
bonding the micropillars to an elastic layer, and
removing the substrate,
wherein the elastic layer has an elasticity that is greater than an elasticity of the micropillars.

11. The method of claim 10, further comprising:
disposing a seed layer over the substrate, and
removing the seed layer.

12. The method of claim 10, further comprising thermally annealing the micropillars.

13. The method of claim 10, further comprising disposing an adhesion layer over the substrate.

14. The method of claim 10, further comprising disposing silica over the micropillars.

15. The method of claim 10, further comprising forming the elastic layer.

16. The method of claim 10, wherein disposing the ferromagnetic material comprises at least one of an electroplating process, a chemical vapor deposition process, a plasma vapor deposition process, and an electroless plating process.

17. A method comprising:
applying a magnetic field to a structure, wherein the structure comprises a plurality of ferromagnetic micropillars disposed over an elastic layer, to change a tilt angle of at least some of the micropillars relative to a normal of the elastic layer,
wherein the elastic layer has an elasticity that is greater than an elasticity of the micropillars.

18. The method of claim 17, wherein the tilt angle of the at least some of the micropillars after the application of the magnetic field is in the range of about 0° to about 60° relative to the normal of the elastic layer.

19. The method of claim 17, wherein the change in the tilt angle of the at least some of the micropillars produces a change in at least one of the surface drag, optical properties, spreading characteristics, wetting characteristics, heat transfer, surface adhesive properties and audio characteristics of the structure.

20. The method of claim 17, wherein the tilt angles among the at least some of the micropillars relative to the normal of the elastic layer after the application of the magnetic field are uniform.

* * * * *